(12) United States Patent
Cheng et al.

(10) Patent No.: US 7,985,264 B2
(45) Date of Patent: Jul. 26, 2011

(54) CUSHION STRUCTURE OF ARTIFICIAL KNEE JOINT

(76) Inventors: Chia-Pao Cheng, Shu Lin (TW);
Fu-Kuo Wu, Shu Lin (TW)

( * ) Notice: Subject to any disclaimer, the term of this patent is extended or adjusted under 35 U.S.C. 154(b) by 142 days.

(21) Appl. No.: 12/507,080

(22) Filed: Jul. 22, 2009

(65) Prior Publication Data
US 2011/0022185 A1    Jan. 27, 2011

(51) Int. Cl.
*A61F 2/64* (2006.01)
*A61F 2/68* (2006.01)

(52) U.S. Cl. ........................................................... 623/44

(58) Field of Classification Search ............... 623/39–46
See application file for complete search history.

(56) References Cited

U.S. PATENT DOCUMENTS

| | | | |
|---|---|---|---|
| 6,086,616 A * | 7/2000 | Okuda et al. | 623/44 |
| 2004/0107008 A1* | 6/2004 | Veen | 623/39 |
| 2005/0143839 A1* | 6/2005 | Chen et al. | 623/39 |
| 2009/0088867 A1* | 4/2009 | Andrysek | 623/39 |
| 2010/0100197 A1* | 4/2010 | Kremser et al. | 623/38 |

* cited by examiner

*Primary Examiner* — Bruce E Snow
(74) *Attorney, Agent, or Firm* — Leong C. Lei

(57) ABSTRACT

An artificial knee joint includes a joint support having upper and lower ends jointed to outside links and an upper link respectively; a brake block having upper and lower jointing holes respectively jointing a lower end of the upper link and a connector, and having an upper portion forming a positioning slot; a hydraulic cylinder arranged inside the brake block and having an upper end coupled to the joint support; a connector having a lower portion connected to a shank and an upper end portion through which a positioning axle extends; and outside links having an upper end jointed to an upper jointing hole of the joint support and a lower end jointed to a jointing hole of the connector. A cylinder barrel, a piston, a resilient element, and an adjusting bolt are arranged inside the connector and the piston is set against a lower end of the brake block.

4 Claims, 3 Drawing Sheets

CUSHION STRUCTURE OF ARTIFICIAL KNEE JOINT

TECHNICAL FIELD OF THE INVENTION

The present invention generally relates to a cushion structure of an artificial knee joint, and more particularly to a connector that connects an artificial knee joint and a shank and comprises a piston cooperating a resilient element to allow a user of an artificial limb to move in comply with road surface when he or she is walking or slightly bending.

DESCRIPTION OF THE PRIOR ART

With the mature of development of medical mechanical structures, a limb disabled person may rely on various mechanical devices to improve maneuverability and result of rehabilitation thereof. Those mechanical devices are so developed as to mimic the operation of joint and muscles of human body to pursue artificial movement of human in a natural way. Taking walking of leg joints as an example, all the joints of the leg and sole that are located below the hip joint must move in such a way to comply with the road surface, such as a stepped surface, a wet and slippery surface, an inclined surface, and an uneven surface, in order to maintain balanced and in proper contact with the ground surface. Emphasis of the conventional lower limb knee joint is focused on the control of the knee joint alone and the cooperation of the portion of the leg below the shank with the knee joint is hardly controlled, so that a user of an artificial limb hardly perceives a feedback from the ground surface when he or she is walking. An included angle is formed between the sole heel and the ground and the sole cannot timely change posture to comply with the ground surface. Further, impact force induced by contacting the ground surface may make the user of the artificial limb uncomfortable. Apparently, improvement in these respects is needed.

SUMMARY OF THE INVENTION

In view of the above problems, the present invention aims to provide an improvement on the conventional artificial knee joint by arranging a cushion structure in a connector of the artificial knee joint so as to allow an artificial limb user to walk and stand in such a way to comply with ground surface and to reduce impact force acting thereon.

The present invention provides a cushion structure of an artificial knee joint, comprising a joint support having an upper end jointed to upper ends of outside links and a lower end jointed to an upper end of an upper link; a brake block having an upper jointing hole jointing a lower end of the upper link and a lower end jointing a connector, an upper portion having a rear section forming a positioning slot; a hydraulic cylinder arranged inside the brake block and having an upper piston-rod end coupled inside the joint support; a connector having a lower portion connected to a shank and an upper end portion having a rear section through which a positioning axle extends; outside links having an upper end jointed to an upper jointing hole of the joint support and a lower end jointed to a jointing hole of the connector. Since an artificial limb user cannot perceives feedbacks from a road surface when he or she is walking, an unnatural included angle is often formed between the sole and the ground surface and an impact force induced may make the artificial limb user uncomfortable. To cope with such problems, the present invention arranges a cylinder barrel, a piston, a resilient element, and an adjusting bolt inside the connector and sets the piston against a lower end of the brake block, so that when the knee joint slight bends and the brake block slightly and rearward rotates, the lower end of the brake block is supported by the piston that is subjected to a resilient force of the resilient element to thereby provide a cushioning reaction force, whereby the artificial limb user is allowed to have the sole thereof complying with ground surface when walking or slightly bending and the impact force induced when contacting the ground surface is reduced to thereby realize more comfortable and natural pacing.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

Figure 1:
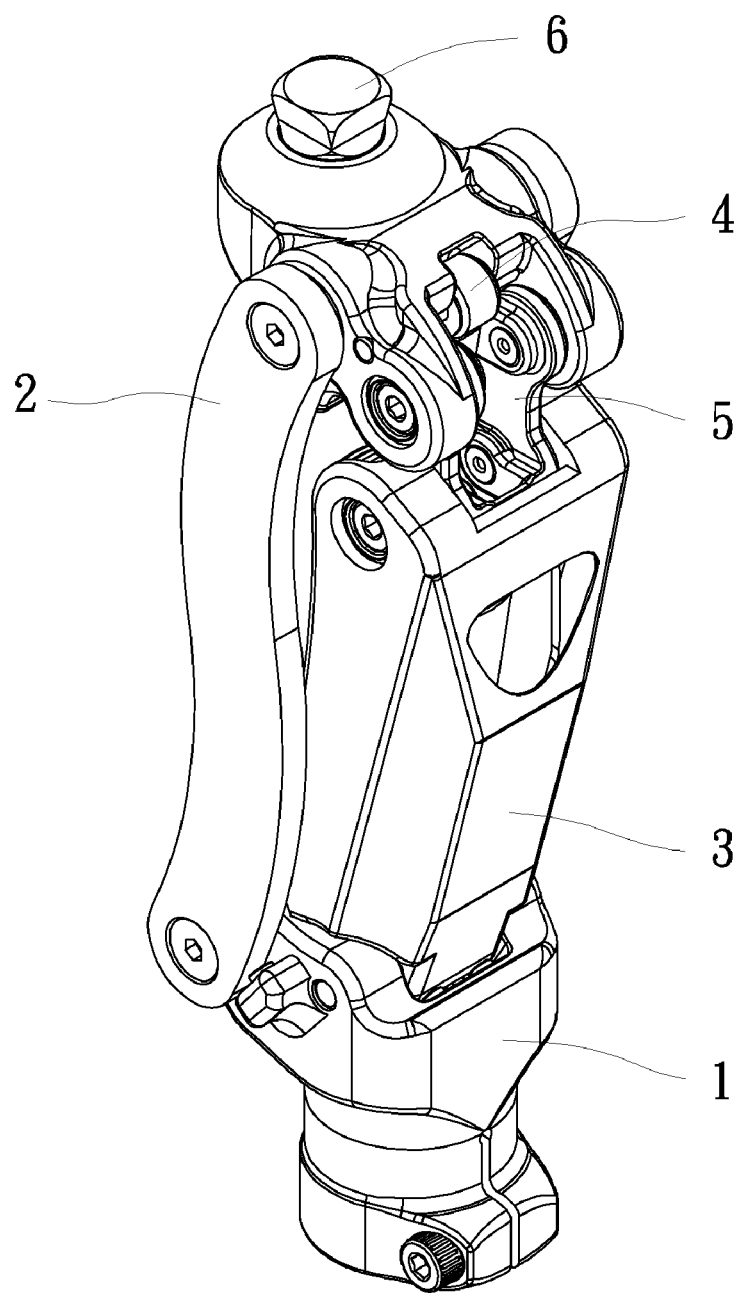
FIG. 1 shows a perspective view of the present invention.

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

The present invention will now be described in respect of the structure, functions and other features thereof with reference to the attached drawings in order to facilitate understanding of the present invention. The present invention provides a cushion structure of an artificial knee joint, which, as shown in FIGS. 1-3, comprises a connector 1, at least one (preferably two) outside link 2, a brake block 3, a hydraulic cylinder 4, an upper link 5, and a joint support 6.

Figure 2:
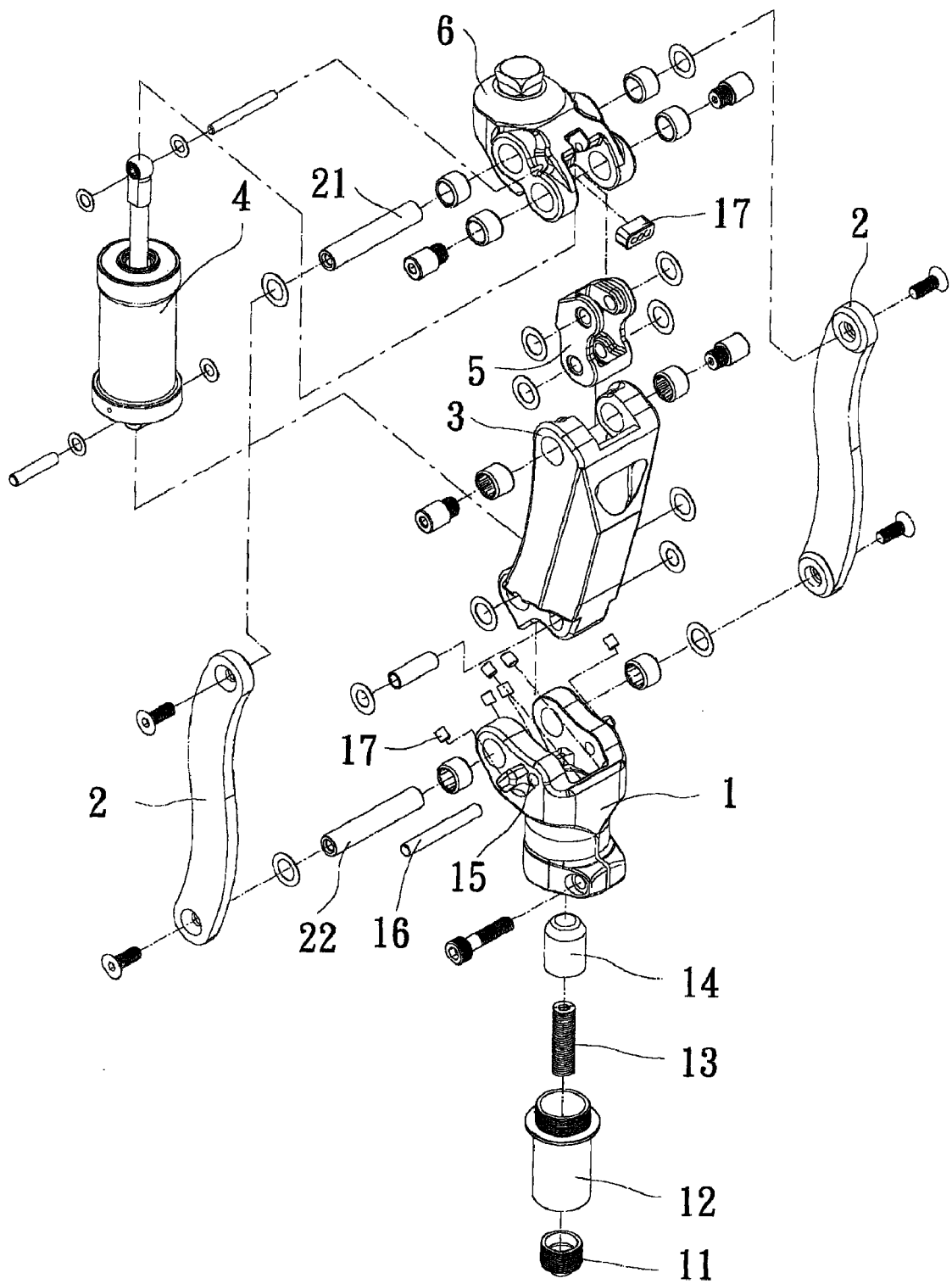
FIG. 2 shows an exploded view of the present invention.

As shown in FIGS. 1 and 2, the joint support 6 has upper and lower portions respectively forming jointing holes. The upper jointing hole joints an upper end of each outside link 2 and the lower jointing hole joints an upper end of the upper link 5. The brake block 3 has upper and lower portions respectively forming jointing holes, of which the upper jointing hole joints a lower end of the upper link 5 and the lower jointing hole joints an upper end of the connector 1. The hydraulic cylinder 4 is arranged inside the brake block 3 and has an upper piston-rod end coupled inside the joint support 6. The connector 1 forms a jointing hole in the upper end thereof and has a lower portion connected to an artificial shank and an upper end portion forming in a rear section thereof a positioning axle bore 15 for receiving and supporting a positioning axle 16. Each outside link 2 is jointed to the upper jointing hole of the joint support 6 with the upper end thereof by a penetrating pivot 21 and is also jointed to the upper jointing hole of the connector 1 with a lower end thereof by a penetrating pivot 22. One or more shock absorption blocks 17 are arranged between the brake block 3 and the connector 1. Also, one or more shock absorption blocks 17 are arranged between the joint support 6 and the upper link 5.

Figure 3:
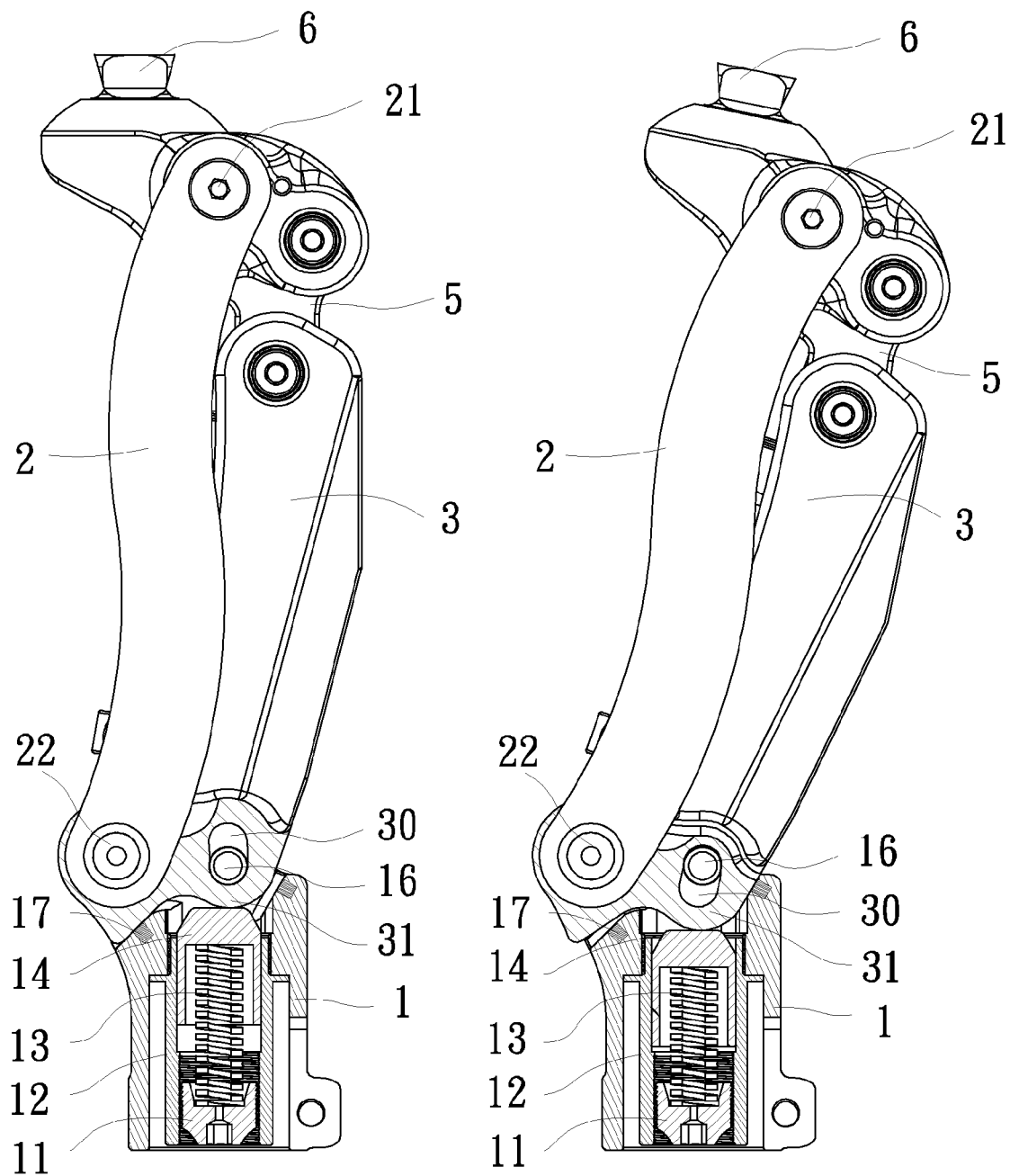
FIG. 3 shows cross-sectional views of the present invention to demonstrate the operation of the present invention.

As shown in FIGS. 2 and 3, the lower portion of the connector 1 is connectable to an artificial shank. Arranged inside the connector 1 are an adjusting bolt 11, a cylinder barrel 12 having a lower open section receiving and mating there adjusting bolt 11 therein, a resilient element 13, and a piston 14 movably received in an upper open section of the cylinder barrel 12 with the resilient element 13 set between the adjusting bolt 11 and the piston 14. The piston 14 is set against a lower end 31 of the brake block 3 so that when the knee joint slight bends or when a sole of the shank contacts a fixed surface, such as ground, within a movement range defined by movement of the positioning axle 16 within a width of a positioning slot 30, the brake block 3 is allowed to rotate about the lower pivot 22, preferably in such a way that a range of angular displacement of the rotation is proportional to the movement range, and drive the piston 14 downward thereby compressing the resilient element 13, which together with the arrangement of the shock absorption blocks 17, provides a reaction against the brake block 3 and alleviate the impact induced by contact with the ground so as to allow the sole to comply with the inclination of the ground, if any, for adopting a comfortable pacing fashion.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

We claim:

1. An artificial knee joint, comprising:
    a joint support, which forms an upper jointing hole that joints an upper end of an outside link with an upper pivot penetrating therethrough and a lower jointing hole that joints an upper end of an upper link;
    a brake block, which forms an upper jointing hole that joints a lower end of the upper link and a lower jointing hole that joints an upper end of a connector, the brake block forming a positioning slot that movably receives a positioning axle extending therethrough;
    a hydraulic cylinder, which has an upper piston-rod end coupled inside the joint support and a lower cylinder-barrel end arranged inside the brake block;
    said connector, which forms a jointing hole in an upper end thereof and has a lower portion connected to an artificial shank and an upper end portion forming in a rear section thereof a positioning axle bore for receiving and supporting the positioning axle; and
    a second outside link which has an upper end jointed to the upper jointing hole of the joint support by the upper pivot extending therethrough and a lower end jointed to the jointing hole of the connector by a lower pivot extending therethrough;
    characterized in that the connector contains therein a cylinder barrel having an upper open section movably receiving a piston therein and a lower open section receiving and mating an adjusting bolt therein, a resilient element being set between the adjusting bolt and the piston, the piston being set against a lower end of the brake block, whereby the resilient element and the piston apply a reaction force to the lower end of the brake block for cushioning purposes.

2. The artificial knee joint according to claim 1, wherein the brake block and the connector comprise a shock absorption block set therebetween.

3. The artificial knee joint according to claim 1, wherein the joint support and the upper link comprise a shock absorption block set therebetween.

4. The artificial knee joint according to claim 1, wherein the brake block is rotatable within a range proportional to a width of the positioning slot within which the positioning axle is allowed to move.

* * * * *